United States Patent
Dane et al.

(10) Patent No.: US 10,669,956 B2
(45) Date of Patent: Jun. 2, 2020

(54) FUEL TYPE PREDICTION FROM MASS FLOW MEASUREMENTS AND THERMAL CONDUCTIVITY SENSOR

(71) Applicant: Cummins Inc., Columbus, IN (US)

(72) Inventors: Marten H. Dane, Columbus, IN (US); Shu Li, Columbus, IN (US)

(73) Assignee: Cummins Inc., Columbus, IN (US)

( * ) Notice: Subject to any disclaimer, the term of this patent is extended or adjusted under 35 U.S.C. 154(b) by 0 days.

(21) Appl. No.: 16/098,692

(22) PCT Filed: May 9, 2016

(86) PCT No.: PCT/US2016/031426
§ 371 (c)(1),
(2) Date: Nov. 2, 2018

(87) PCT Pub. No.: WO2017/196293
PCT Pub. Date: Nov. 16, 2017

(65) Prior Publication Data
US 2019/0120151 A1   Apr. 25, 2019

(51) Int. Cl.
*G01F 1/68* (2006.01)
*F02D 41/00* (2006.01)
(Continued)

(52) U.S. Cl.
CPC .......... *F02D 41/0027* (2013.01); *F01K 13/02* (2013.01); *F01K 23/10* (2013.01); *F01K 23/101* (2013.01); *F02B 43/00* (2013.01); *F02C 3/22* (2013.01); *F02C 3/34* (2013.01); *F02C 9/28* (2013.01); *F02C 9/40* (2013.01);
(Continued)

(58) Field of Classification Search
CPC .. F02D 41/00; F02D 41/0025; F02D 41/0027; F02D 2200/0611; F02D 2200/0612; F02M 21/02; F02M 21/0209; F02M 21/0212; F02M 21/0215; F02B 43/00; F02B 2043/103; G01F 1/88
See application file for complete search history.

(56) References Cited

U.S. PATENT DOCUMENTS 4,685,331 A   8/1987   Renken et al.
4,945,882 A   8/1990   Brown et al.
(Continued)

OTHER PUBLICATIONS

International Search Report and Written Opinion issued by the ISA/US, Commissioner for Patents, dated Aug. 11, 2016, for related International Application No. PCT/US2016/031426; 9 pages.
(Continued)

*Primary Examiner* — Erick R Solis
(74) *Attorney, Agent, or Firm* — Faegre Drinker Biddle & Reath LLP

(57) ABSTRACT

The present disclosure provides a method for predicting a fluid type, comprising sensing, by a first sensor, mass flow data of a fluid in an engine, wherein the first sensor operates based on a first fluid property; sensing, by a second sensor, mass flow data of the fluid, wherein the second sensor operates based on a second fluid property; and detecting, by a logic circuit of a controller, a percent difference in the mass flow data provided by the first and second sensors, the percent difference indicating that the fluid is comprised of at least a first fluid type.

26 Claims, 7 Drawing Sheets

(51) Int. Cl.

| | |
|---|---|
| *F02C 9/28* | (2006.01) |
| *F02C 3/22* | (2006.01) |
| *F02C 9/40* | (2006.01) |
| *F02D 19/02* | (2006.01) |
| *F02D 19/06* | (2006.01) |
| *F02C 3/34* | (2006.01) |
| *F01K 23/10* | (2006.01) |
| *F01K 13/02* | (2006.01) |
| *F02M 21/02* | (2006.01) |
| *F02B 43/00* | (2006.01) |
| *G01F 1/692* | (2006.01) |
| *G01F 1/696* | (2006.01) |
| *G01N 11/00* | (2006.01) |
| *G01N 25/00* | (2006.01) |
| *G01N 33/28* | (2006.01) |
| *F02D 41/14* | (2006.01) |
| *F02B 43/10* | (2006.01) |
| *G01F 1/88* | (2006.01) |

(52) U.S. Cl.
CPC ....... *F02D 19/029* (2013.01); *F02D 19/0634* (2013.01); *F02D 19/0647* (2013.01); *F02D 41/0025* (2013.01); *F02M 21/0209* (2013.01); *F02M 21/0212* (2013.01); *F02M 21/0215* (2013.01); *G01F 1/68* (2013.01); *G01F 1/692* (2013.01); *G01F 1/696* (2013.01); *G01N 11/00* (2013.01); *G01N 25/00* (2013.01); *G01N 33/2829* (2013.01); *F02B 2043/103* (2013.01); *F02D 41/1496* (2013.01); *F02D 2200/0602* (2013.01); *F02D 2200/0611* (2013.01); *F02D 2200/0612* (2013.01); *F02D 2200/0614* (2013.01); *F02D 2400/08* (2013.01); *F05D 2270/306* (2013.01); *F05D 2270/44* (2013.01); *G01F 1/88* (2013.01); *Y02T 10/36* (2013.01)

(56) References Cited

U.S. PATENT DOCUMENTS

| | | | |
|---|---|---|---|
| 5,311,447 A | 5/1994 | Bonne | |
| 5,697,346 A | 12/1997 | Beck | |
| 5,701,853 A | 12/1997 | Takahashi | |
| 6,442,996 B1 | 9/2002 | Thurston et al. | |
| 7,653,497 B2 * | 1/2010 | Cline | G01J 3/02 |
| | | | 702/30 |
| 7,752,884 B2 * | 7/2010 | Huang | G01F 1/668 |
| | | | 73/23.2 |
| 7,752,885 B2 * | 7/2010 | Huang | G01F 1/667 |
| | | | 73/23.2 |
| 8,667,839 B2 | 3/2014 | Kimura | |
| 2003/0136175 A1 | 7/2003 | Saikalis et al. | |
| 2004/0158411 A1 * | 8/2004 | Morrow | G01N 29/024 |
| | | | 702/27 |
| 2005/0143937 A1 | 6/2005 | Morrow et al. | |
| 2009/0193788 A1 | 8/2009 | Szepek et al. | |
| 2009/0287520 A1 | 11/2009 | Zimmerman | |
| 2011/0077872 A1 | 3/2011 | Loui et al. | |
| 2011/0209526 A1 | 9/2011 | Wagner | |
| 2012/0187688 A1 | 7/2012 | Draper | |
| 2014/0060176 A1 | 3/2014 | Mais et al. | |
| 2014/0209070 A1 | 7/2014 | Gleeson et al. | |

OTHER PUBLICATIONS

International Preliminary Report on Patentability issued by the IPEA/US, dated May 16, 2018, for related International Application No. PCT/US2016/031426; 6 pages.

* cited by examiner

FUEL TYPE PREDICTION FROM MASS FLOW MEASUREMENTS AND THERMAL CONDUCTIVITY SENSOR

CROSS-REFERENCE TO RELATED APPLICATION

This application is a national phase filing of PCT International Application Serial No. PCT/US2016/031426, filed May 9, 2016, the disclosure of which is expressly incorporated herein by reference.

FIELD OF THE DISCLOSURE

The present disclosure generally relates to predicting fuel type and composition of natural gas fuel and more specifically to an apparatus and methods for predicting the fuel type and composition based on at least mass flow sensor measurements and thermal conductivity sensor measurements.

BACKGROUND OF THE DISCLOSURE

Natural gas is a naturally occurring gas mixture that is comprised of several different types of gas. Many natural gas fuel types are primarily mixtures of varying percent compositions that include gases such as: $CH_4$ (methane), $C_3H_8$ (propane), $C_2H_6$ (ethane), $C_4H_{10}$ (butane), $O_2$ (oxygen), $N_2$ (nitrogen), $H_2S$ (hydrogen sulfide), and $CO_2$ (carbon dioxide). There are a variety of professional suppliers of natural gas. In some instances natural gas supplied from these various suppliers may have a similar composition but will rarely be entirely the same. Accordingly, with different gas suppliers each supplying natural gas, the exact composition at any natural gas production site will vary among different regions.

Having information relating to the chemical composition of natural gas supplied by a particular gas source can be valuable for engine manufacturers and engine control system designers. For example, the fractions of species within certain natural gas supplies have large impacts on the knock, NOx, and lean burning limit capability of the engine. Hence, a need exists for an apparatus and method(s) for reliably predicting fuel type and composition of natural gas fuel provided by the various suppliers. Accordingly, the present disclosure provides an apparatus and method(s) for predicting fuel type and composition of natural gas based on sensitivities associated with measuring devices commonly used in vehicle engine applications.

SUMMARY OF THE DISCLOSURE

In one embodiment, the present disclosure provides a fluid type prediction system, comprising a first sensor that provides a first mass flow measurement of a fluid in an engine, wherein the first sensor is sensitive to at least a first property of the fluid; and a second sensor that provides a second mass flow measurement of the fluid, wherein the second sensor is sensitive to at least a second property of the fluid; a controller configured to detect a difference between the first and the second mass flow measurements indicating a presence of at least a first fluid type in the fluid, and to adjust a performance characteristic of the engine in response to detecting the difference between the first and the second mass flow measurements. In one aspect of this embodiment, the system is configured to detect a percentage of the first fluid type in the fluid in response to the difference between the first and the second mass flow measurements exceeding a threshold difference. In a variant of this aspect, the system further comprises a third sensor that provides a measurement of a characteristic of the fluid, wherein the characteristic indicates a percentage of a second fluid type in the fluid. In a variant of this variant, the percentage of the first fluid type and the percentage of the second fluid type are used to determine a presence of a third fluid type in the fluid and to determine a percentage of the third fluid type in the fluid. In another variant of this variant, the first sensor is an orifice delta pressure mass flow sensor, the second sensor is a hot film mass flow sensor, and the third sensor is a thermal conductivity sensor. In yet another variant of this variant, the fluid is natural gas fuel comprising at least one of methane, propane, carbon dioxide, and combinations thereof, and the characteristic of the fluid is a thermal conductivity of the fluid. In yet another aspect, the fluid is natural gas fuel, the first property is molecular weight, and the second property is at least one of viscosity and thermal conductivity. In yet another aspect, the system is configured to estimate a percentage of one or more fluid types in the fluid.

In another embodiment, the present disclosure provides a fluid type prediction system, comprising a controller comprising at least one processor and memory; and a first interface coupled to the controller, the first interface configured to receive parameter signals corresponding to a mass flow measurement of a fluid in an engine, the parameter signals being provided by at least a first sensor and a second sensor; wherein the memory comprises instructions that when executed by the at least one processor causes the controller to detect a difference between the mass flow measurement provided by the first sensor and the mass flow measurement provided by the second sensor, the difference indicating the presence of at least a first fluid type in the fluid, and to adjust a performance characteristic of the engine in response to detecting the difference between the mass flow measurements provided by the first and second sensors. In one aspect of this embodiment, the system is configured to detect a percentage of the first fluid type in the fluid in response to the difference between the mass flow measurements provided by the first sensor and the second sensor exceeding a threshold difference. In another aspect, the first sensor is sensitive to at least a first property of the fluid and the second sensor is sensitive to at least a second property of the fluid. In a variant of this aspect, the fluid is natural gas fuel, the first property is molecular weight, and the second property is at least one of viscosity and thermal conductivity.

In yet another aspect, the controller comprises a second interface configured to provide control signals to at least the first sensor and the second sensor to cause the first and second sensors to provide the mass flow measurement to the controller. In yet another aspect, the first interface receives parameter signals provided by a third sensor, the parameter signals indicating a characteristic of the fluid, wherein the characteristic indicates a percentage of a second fluid type in the fluid. In a variant of this aspect, the controller uses the percentage of the first fluid type and the percentage of the second fluid type to determine a presence of a third fluid type in the fluid and to determine a percentage of the third fluid type in the fluid. In another variant of this aspect, the first sensor is an orifice delta pressure mass flow sensor, the second sensor is a hot film mass flow sensor, and the third sensor is a thermal conductivity sensor.

In yet another embodiment, the present disclosure provides a method for predicting a fluid type, comprising providing, by a first sensor, a mass flow measurement of a fluid in an engine, wherein the first sensor is sensitive to at least a first property of the fluid; providing, by a second sensor, a mass flow measurement of the fluid, wherein the second sensor is sensitive to at least a second property of the fluid; detecting, by a logic circuit of a controller, a difference between the mass flow measurement provided by the first sensor and the second sensor, the difference indicating a presence of at least a first fluid type in the fluid; and adjusting, by the logic circuit, a performance characteristic of the engine in response to detecting the difference between the mass flow measurement provided by the first sensor and the second sensor. In one aspect of this embodiment, the method further comprises, detecting a percentage of the first fluid type in the fluid in response to the difference in the mass flow measurement provided by the first sensor and the second sensor exceeding a threshold difference. In a variant of this aspect, the method further comprises, sensing, by a third sensor, a characteristic of the fluid; detecting, based on the characteristic, the presence of at least a second fluid type in the fluid; and determining a percentage of the second fluid type in the fluid. In a variant of this variant, the method further comprises, using the percentage of the first fluid type and the percentage of the second fluid type to determine a presence of a third fluid type in the fluid and to determine a percentage of the third fluid type in the fluid. In another variant of this variant, the first sensor is an orifice delta pressure mass flow sensor, the second sensor is a hot film mass flow sensor, the third sensor is a thermal conductivity sensor, the first property is molecular weight, and the second property is at least one of viscosity and thermal conductivity.

In yet another embodiment, the present disclosure provides a fluid type prediction system comprising a controller comprising at least one processor and memory; and an interface coupled to the controller, the interface configured to receive parameters indicating a mass flow measurement of a fluid in an engine; wherein the memory comprises instructions that when executed by the at least one processor causes the controller to detect a difference between a mass flow measurement provided by a first sensor and a mass flow measurement provided by a second sensor, the difference indicating the presence of at least a first fluid type in the fluid; and wherein a performance characteristic of the engine is adjusted in response to the controller detecting a difference between the mass flow measurements provided by the first and second sensors. In one aspect of this embodiment, the parameters received by the interface are provided by at least the first sensor and the second sensor. In a variant of this aspect, the interface is further configured to receive a measurement of a characteristic of the fluid, the characteristic indicating a percentage of a second fluid type in the fluid, and the measurement being provided by a third sensor. In a variant of this variant, the first sensor is an orifice delta pressure mass flow sensor, the second sensor is a hot film mass flow sensor, and the third sensor is a thermal conductivity sensor. In another aspect, the system is configured to at least one of estimate a percentage of one or more fluid types in the fluid and detect a percentage of the first fluid type in the fluid in response to the difference between the first and the second mass flow measurements exceeding a threshold difference. In yet another aspect, the performance characteristic include at least one of fuel injection timing, air-to-fuel ratio, charge flow rate and quantity, spark ignition timing, and adjusting the operation of one or more components of the engine.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein.

DETAILED DESCRIPTION OF EMBODIMENTS

The embodiments disclosed herein are not intended to be exhaustive or to limit the disclosure to the precise forms disclosed in the following detailed description. Rather, the embodiments were chosen and described so that others skilled in the art may utilize their teachings. The following description is merely exemplary in nature and is in no way intended to limit the various application or uses of the disclosure. As used herein, the phrase at least one of A, B, and C should be construed to mean a logical (A or B or C), using a non-exclusive logical OR. It should be understood that steps within a method may be executed in a different order without altering the principles of the present disclosure. As used herein, the term determiner, or interpreter may refer to an Application Specific Integrated Circuit (ASIC), an electronic circuit, a processor (shared, dedicated, or group) and memory that execute one or more software or firmware programs, a combinational logic circuit, and/or other suitable components that provide the described functionality.

Figure 1:
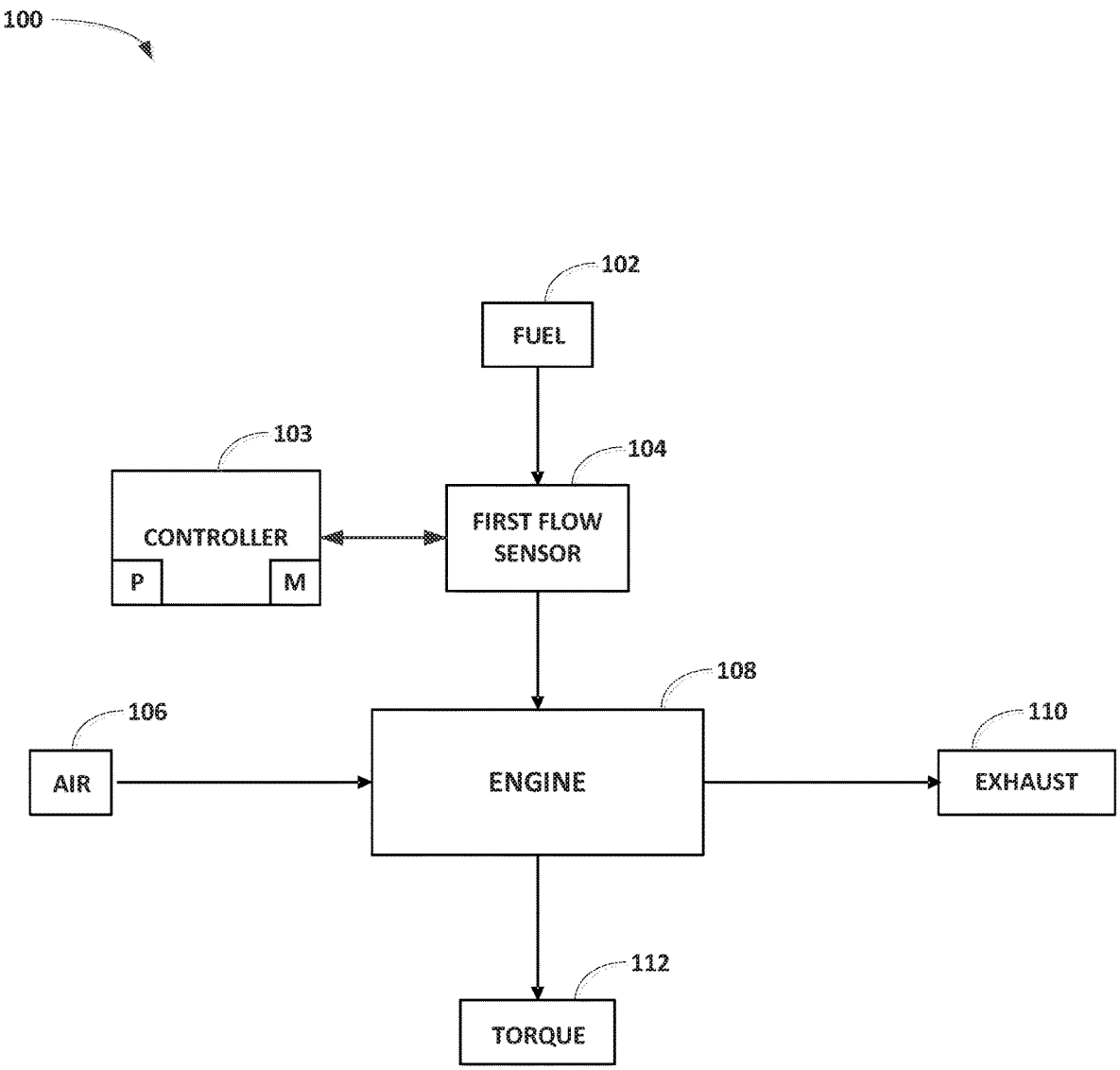
FIG. 1 is a block diagram of an exemplary prior art flow measuring system according to an embodiment of the present disclosure.

Referring now to FIG. 1, a block diagram of an exemplary prior art flow measuring system according to an embodiment of the present disclosure is shown. Flow measuring system 100 (hereinafter "system 100") generally includes fluid or fuel inlet 102, controller 103, first flow sensor 104, air inlet 106, engine 108, exhaust 110, and torque output 112. As shown in the illustrative embodiment of FIG. 1, controller 103 may be electrically and communicably coupled to first flow sensor 104. Controller 103 is generally configured to provide one or more control signals to first flow sensor 104 to cause flow sensor 104 to sense/measure the mass flow of fluid/fuel flowing into engine 108. Likewise, flow sensor 104 may be configured to provide one or more data/parameter signals to controller 103 that indicate the sensed/measured flow rate of fluid or fuel flowing into engine 108. Flow sensor 104 may be a conventional flow sensor generally known to one of ordinary skill. In one embodiment, flow sensor 104 is a hot film mass flow sensor (e.g., Hitachi Gas Mass Flow Sensor) that operates, in part, based on design sensitivities which are responsive to at least a first fluid property of the fluid being sensed/measured. In various embodiments of the present disclosure, a fluid property may be any one of viscosity of the fluid, thermal conductivity of the fluid, or both. The fluid property may also be the molecular weight of the fluid. In one embodiment, the first fluid property is one of the thermal conductivity of the fluid, the viscosity of the fluid, and/or a combination of both thermal conductivity and viscosity of the fluid. In the present disclosure, the thermal conductivity of the fluid may be also described as a characteristic of the fluid rather than a property of the fluid. Engine 108 generally operates by combusting a fluid mixture comprising air supplied by air let 106 and fuel supplied by fuel inlet 102 to produce drive torque 112 for an exemplary vehicle. Exhaust 110 provides a flow path for exhaust gas produced as a result of the combustion of exemplary fuels such as natural gas, gasoline and diesel.

As discussed above, natural gas fuels tend to vary in composition depending on the location of the fuel source. Natural gas fuels dispensed from a single source location may also vary in composition over time. Constituent changes in the composition of natural gas fuels include, for example, changes in the amount of methane, propane, and carbon dioxide present in the fuel. Generally, natural gas fuel types may be broken into two segments, either low Methane Number (MN) (e.g., natural gas blends comprised of propane) or low British Thermal Units (BTUs) (e.g., natural gas blends comprised of diluents such as carbon dioxide). Manufacturers of natural gas engines sometimes use methane number (MN) or motor octane number (MON) for specification of gas quality requirements. Both the MON and the MN are measures of the knock resistance of the fuel with the difference being the reference fuels used. As indicated above, systems that can consistently and reliably provide information relating to the chemical composition of natural gas fuels supplied by a particular fuel source can be valuable for engine manufacturers and engine control system designers. For example, as indicated above, the fractions of species within certain natural gas fuel supplies have large impacts on the knock, NOx, and lean burning limit capability of a natural gas engine, such as engine 108. Accordingly, the present disclosure provides a sensing and measurement system and method for detecting and indicating the presence and fraction/percentage of individual gases that comprise natural gas fuels dispensed at a particular location.

Figure 2:
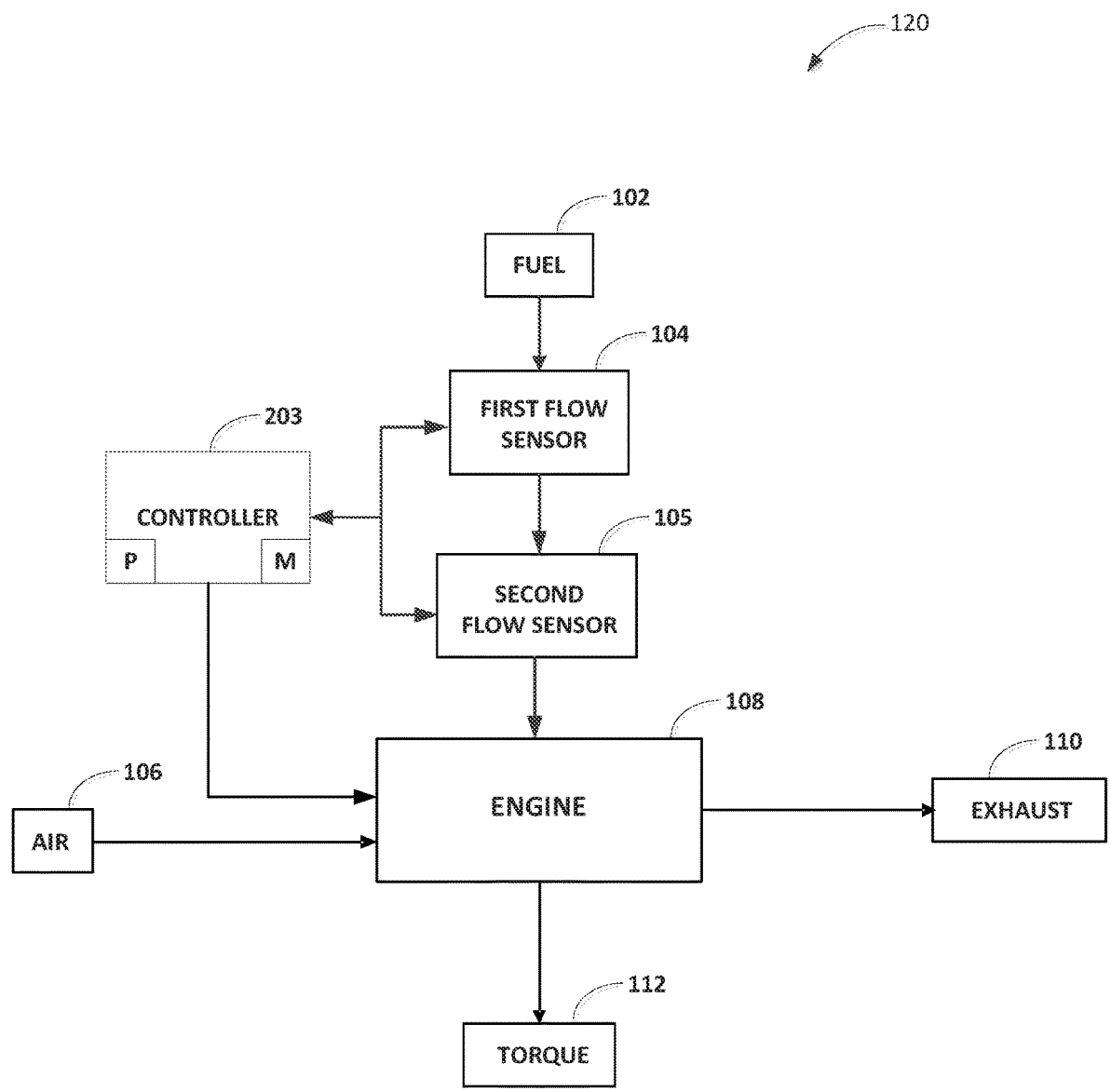
FIG. 2 is a block diagram of a fluid type prediction system comprising at least two sensors according to an embodiment of the present disclosure.

Referring now to FIG. 2, a block diagram of a fluid type prediction system comprising at least two sensors according to an embodiment of the present disclosure is shown. Flow measuring system 120 (hereinafter "system 120") generally includes first flow sensor 104, a second flow sensor 105, and a controller 203. Much like flow sensor 104 described above, flow sensor 105 may be configured to provide one or more data/parameter signals to controller 203 that indicate the sensed/measured flow rate of fluid or fuel flowing into engine 108. Similar to flow sensor 104, flow sensor 105 may also be a conventional flow sensor generally known to one of ordinary skill. In one embodiment, flow sensor 105 is an orifice delta pressure mass flow rate measurement sensor that operates, in part, based on design sensitivities which are responsive to a second fluid property of the fluid being sensed/measured. In one aspect of this embodiment, the second fluid property is the molecular weight of the fluid. Controller 203 is generally configured to provide one or more control signals to at least one of flow sensor 104 and flow sensor 105 to cause at least one of sensor 104 and sensor 105 to sense/measure the mass flow of fluid/fuel flowing into engine 108. Likewise, flow sensors 104, 105 may be configured to provide one or more data/parameter signals to controller 203 that indicate the sensed/measured flow rate of fluid or fuel flowing into engine 108.

In the illustrative embodiment of FIG. 2, flow sensor 104 of system 120 senses, measures and/or provides a mass flow rate measurement of a fluid (fuel) being supplied to engine 108. In one embodiment, sensor 104 is a hot film mass flow sensor that is sensitive to both the thermal conductivity of the fuel and viscosity of the fuel. Sensor 104 is configured to provide one or more parameter signals to controller 203 that are indicative of the sensed or measured mass flow rate of the supplied fuel. System 120 further includes flow sensor 105 that provides a mass flow rate measurement of the fluid (fuel) being supplied to engine 108. In this embodiment, sensor 105 is an orifice delta pressure mass flow rate measurement sensor that is sensitive to the molecular weight of the fuel. Sensor 105 is likewise configured to provide one or more parameter signals to controller 203 that are indicative of the sensed or measured mass flow rate of the supplied fuel.

As described in more detail herein below, controller 203 receives parameters signals indicative of mass flow rate measurements from each of sensors 104, 105 and executes, for example, comparator logic to detect/determine a percent difference between the flow rate measurement values provided by each of the two sensors 104, 105. According to the present disclosure, and as explained further herein, the detected percent difference between a mass flow rate measurement provided by sensor 104 and a mass flow rate measurement provided by sensor 105 indicates a presence of at least a first fluid type in an exemplary natural gas fuel composition. In one embodiment, controller 203 may provide one or more control signals to engine 108 to adjust at least one performance characteristic of engine 108 in response to detecting a presence of the first fluid type in the natural gas fuel. In various embodiments of the present disclosure, the performance characteristics include, for example, fuel injection timing, air-to-fuel ratio, charge flow rate and quantity, spark ignition timing, etc. Likewise, in various embodiments, adjusting the performance characteristics may include adjusting the operation of one or more components of engine 108.

In various embodiments of the present disclosure, controller 203 may include one or more interpreters and one or more determiners such as, for example, a processor (P) that functionally executes the operations of controller 203. Controller 203 may be a single device or a distributed device, and the functions of the controller may be performed by hardware and/or as computer instructions on a non-transient computer readable storage medium. In the illustrative embodiment of FIG. 2, controller 203 is shown as generally including logic/processor (P) and memory (M). In one embodiment, the logic/processor of controller 203 may be a microprocessor that includes one or more control algorithms or logic which are generally operable to control and manage the overall operation of one or more disclosed systems as well as control/manage the operation of a plurality of sensing devices coupled to an exemplary engine or disposed at various locations within an exemplary vehicle. In one embodiment, the processor P may include one or more microprocessors, microcontrollers, digital signal processors (DSPs), combinations thereof and/or such other devices known to those having ordinary skill in the art that may be configured to process one or more data and/or parameter signals and to provide one or more control signals.

Controller 203 may comprise a plurality of electronic components configured to receive analogue and/or digital input signals from a plurality of sensors coupled to an exemplary vehicle and to engine 108. In one or more alternative embodiments, system 120 (and system 150 described below) may be utilized in a variety of related applications having an engine that operates based on natural gas fuel. For example, in these alternative embodiments, related applications may include power generation systems, industrial equipment, and various other systems and devices which are powered, in part, by one or more natural gas engines such as engine 108. Controller 203 may further include a number of input and output circuits (e.g., interface circuits) adapted for interfacing with the plurality of sensors. In one embodiment, controller 203 may be a known control unit customarily referred to by those of ordinary skill as an electronic or engine control module (ECM), electronic or engine control unit (ECU) or the like, or may alternatively be a control circuit capable of operation as will be described herein. In one embodiment, memory M includes random access memory (RAM), dynamic random access memory (DRAM), and/or read only memory (ROM) or equivalents thereof, that store data and programs that may be executed by processor P and that allow controller 203 to communicate with the above-mentioned components to cause one or more systems to perform the functionality described herein.

As noted briefly above, in certain embodiments, controller 203 includes one or more interpreters and one or more determiners. The description herein including interpreters and determiners emphasizes the structural independence of certain aspects of controller 203, and illustrates one grouping of operations and responsibilities of the controller. Other groupings that execute similar overall operations are understood within the scope of the present disclosure. Interpreters and determiners may be implemented in hardware and/or as computer instructions on a non-transient computer readable storage medium, and may be distributed across various hardware or computer based components. Example and non-limiting implementation elements that functionally execute the operations of controller 203 include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hardwired logic circuits, reconfigurable logic circuits in a particular non-transient state configured according to a specification, any actuator including at least an electrical, hydraulic, or pneumatic actuator, a solenoid, an op-amp, analog control elements (springs, filters, integrators, adders, dividers, gain elements), and/or digital control elements.

In various embodiments of the present disclosure, sensors 104, 105 may be calibrated to provide mass flow rate measurements for a gaseous composition that is pure methane or comprised primarily of methane. As noted above, natural gas fuel types are primarily mixtures of varying percent compositions that include gases such as: $CH_4$ (methane), $C_3H_8$ (propane), $C_2H_6$ (ethane), $C_4H_{10}$ (butane), $O_2$ (oxygen), $N_2$ (nitrogen), $H_2S$ (hydrogen sulfide), and $CO_2$ (carbon dioxide). In various embodiments, an exemplary natural gas fuel composition includes methane, propane, and carbon dioxide. As also noted above, major constituent variations in the composition of natural gas fuels include changes in the amount of methane, propane, and carbon dioxide present in the fuel. Thus, because sensor 104 is sensitive to both the thermal conductivity and viscosity of a particular fluid type and sensor 105 is sensitive to molecular weight of a particular fluid type, the detected percent difference between flow rate measurements of each sensor may be used to detect the presence of, for example, carbon dioxide in the natural gas fuel supplied to engine 108. More particularly, because sensors 104, 105 are calibrated to provide flow rate measurements for a gaseous composition that is pure methane (or primarily methane); each sensor 104, 105 will exhibit errors in flow rate measurements of a natural gas fuel composition that is blended with constituents other than methane. In addition to the errors, there will also be a delta (i.e., percent difference) between the flow rate measurement provide by sensor 104 and the flow rate measurement provided by sensor 105. The percent difference can be used to determine one of: 1) the presence of a first fluid type in the natural gas fuel; 2) the presence of second fluid type in the natural gas fuel; 3) an estimation of the percentage/fraction of the first fluid type in the natural gas fuel; 4) and/or an estimation of the percentage/fraction of the second fluid type in the natural gas fuel.

Figure 3:
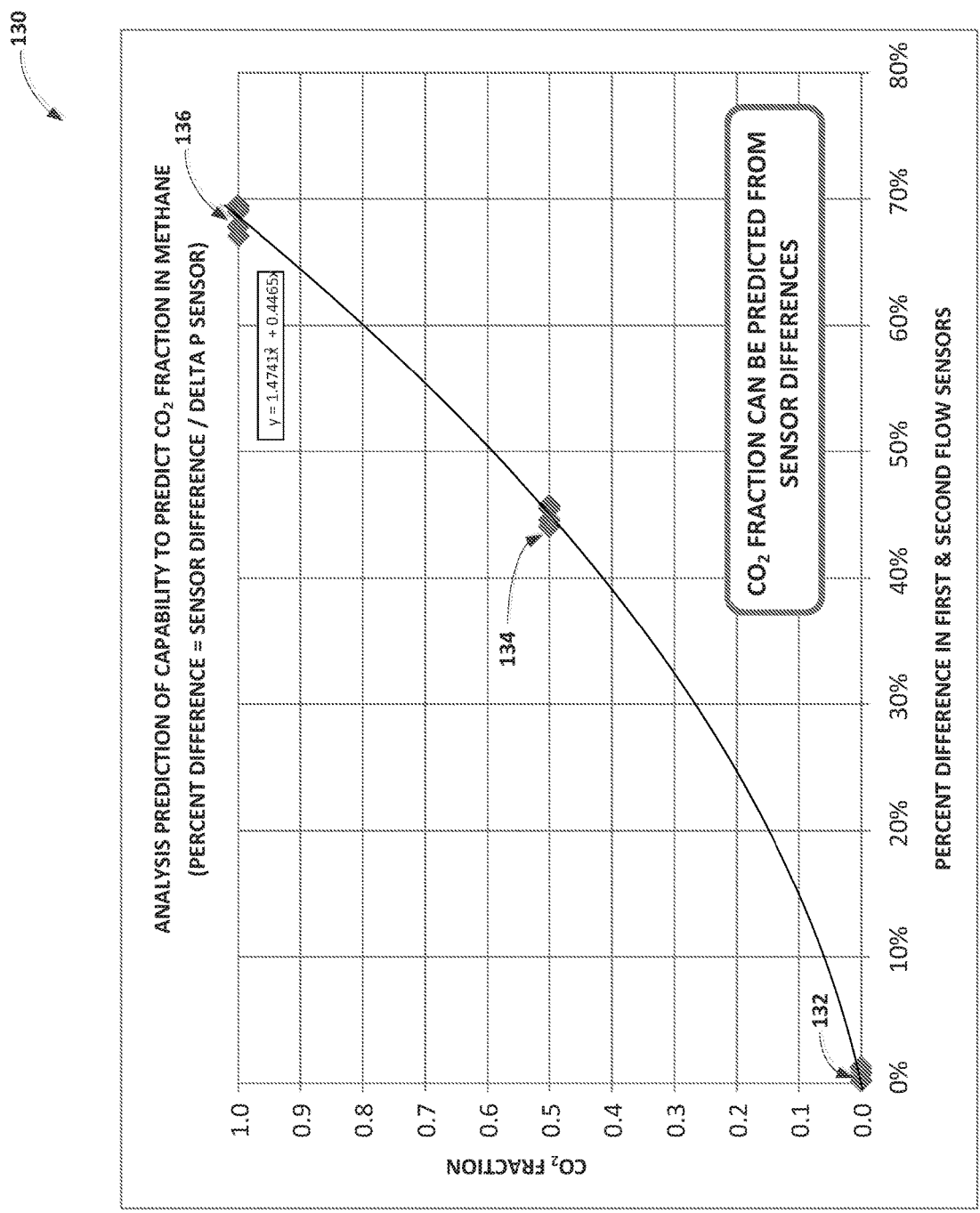
FIG. 3 is a graph that correlates sensor data to a first fluid percentage according to an embodiment of the present disclosure.

FIG. 3 is a graph 130 that correlates a percent difference in flow rate measurement between sensors 104,105 to an estimation of the percentage/fraction of the first fluid type in a natural gas fuel according to an embodiment of the present disclosure. Graph 130 includes first data set 132, second data set 134, and third data set 136. As shown in the illustrative embodiment of FIG. 3, graph 130 presents data indicating analysis predications related to the capability of system 120 to predict/determine/estimate a $CO_2$ fraction (i.e., amount or percentage) in natural gas fuel that is presumed to have some quantity of methane. As illustratively shown, data set 132 shows that a zero percent difference between sensor flow rate measurements provided by sensor 104, 105 indicates that no $CO_2$ fraction is present within the natural gas fuel. Data set 134 shows that an approximately 45 percent difference between sensor flow rate measurements provided by sensor 104, 105 indicates a 0.5 $CO_2$ fraction is present within the natural gas fuel (i.e., fuel is 50% $CO_2$). Lastly, data set 136 shows that an approximately 69 percent difference between sensor flow rate measurements provided by sensor 104, 105 indicates a 1.0 $CO_2$ fraction is present within the natural gas fuel (i.e., fuel is 100% $CO_2$). Accordingly, the sensor data shown in graph 130 indicates that system 120 can be used to predict $CO_2$ fraction in natural gas fuels used to operate a vehicle having engine 108 and system 120 disposed therein.

Figure 4:
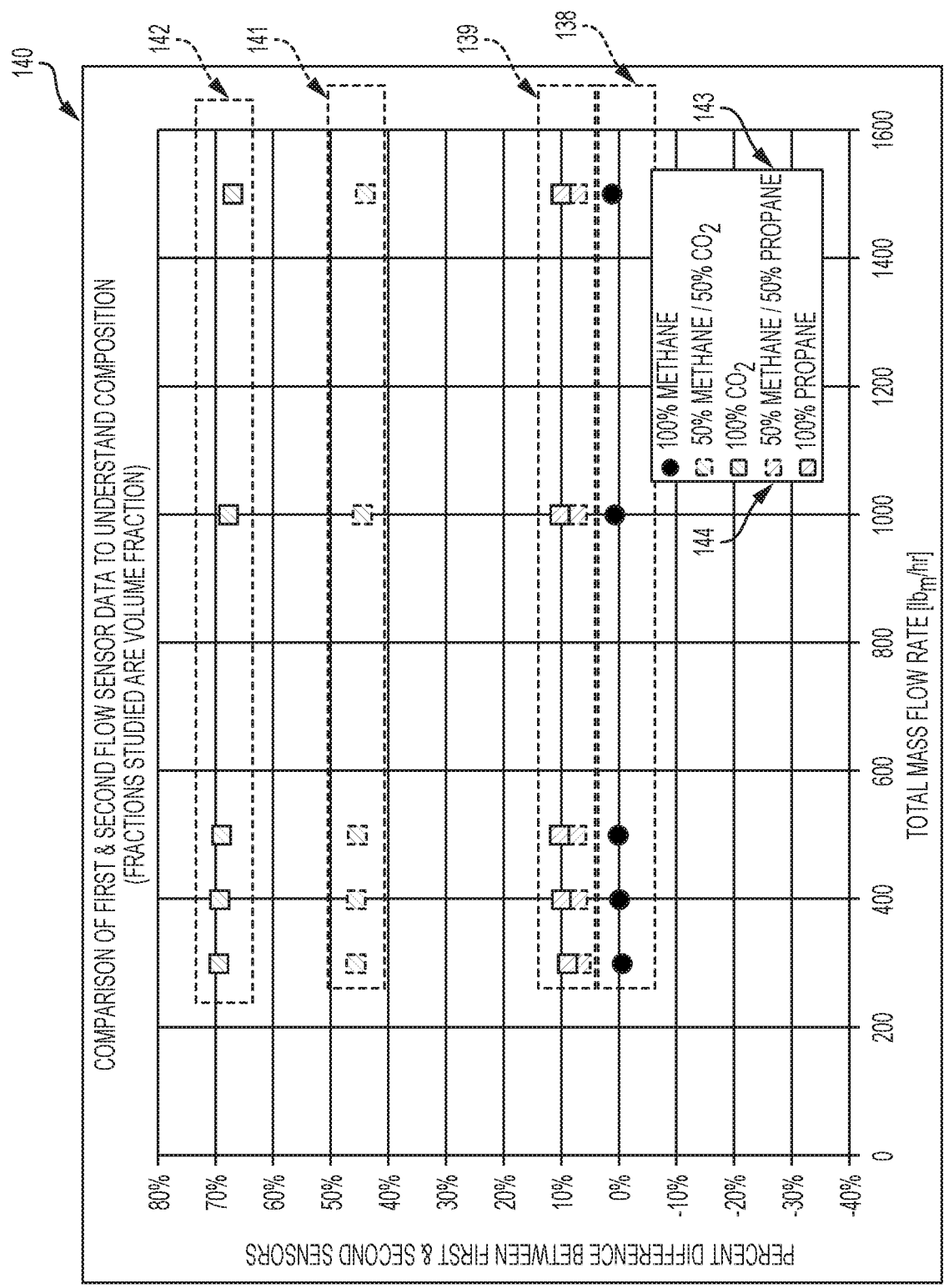
FIG. 4 is a graph that correlates sensor data to mass flow rate for a plurality of fluid compositions according to an embodiment of the present disclosure.

FIG. 4 is a graph 140 that correlates sensor data to mass flow rate for a plurality of fluid compositions 143 according to an embodiment of the present disclosure. More specifically, the sensor data of graph 140 indicates that, for each fluid composition of the plurality of fluid compositions 143, there is a corollary in terms of an expected percent difference between sensors 104, 105 of system 120. Graph 140 includes first data set 138, second data set 139, third data set 141, and fourth data set 142. Graph 140 further includes a graph key/legend 144 that identifies a particular fluid composition and its corresponding graph symbol. As discussed above, in one embodiment, sensors 104, 105 are calibrated to provide mass flow rate measurements for a fluid composition that is pure methane. Hence, because sensors 104, 105 are calibrated for pure methane, each sensor will exhibit errors in flow rate measurements of natural gas fuel blended with constituents other than methane.

In the illustrative embodiment of FIG. 4, first data set 138 shows that a pure methane fuel/fluid composition measured by sensors 104, 105 results in approximately 0% difference between the measured sensor values irrespective of total mass flow rate (as expected since sensors are calibrated for methane). Second data set 139 includes data for two separate fluid compositions and shows that: 1) a fluid composition comprised of 50% methane and 50% propane results in approximately 8% difference between the measured sensor values irrespective of total mass flow rate; and 2) a fluid composition comprised of 100% propane results in approximately 10% difference between the measured sensor values irrespective of total mass flow rate. Third data set 141 shows that a fluid composition comprised of 50% methane and 50% carbon dioxide results in approximately 45% difference between the measured sensor values irrespective of total mass flow rate. Fourth data set 142 shows that a pure carbon dioxide fuel/fluid composition measured by sensors 104, 105 results in approximately 70% difference between the measured sensor values at 200 to 600 total mass flow rate measured in pound-mass per hour ($lb_m$/hr). Fourth data set 142 further shows that, at 1000 $lb_m$/hr to 1500 $lb_m$/hr, a pure carbon dioxide fuel/fluid composition measured by sensors 104, 105 results in approximately 68-69% difference between the measured sensor values.

In one embodiment, system 120 may be configured to detect/estimate a percentage of a first fluid type in the natural gas fuel when the percent difference between the mass flow rate measurements provided by sensor 104 and sensor 105 exceeds a threshold percent difference. In one aspect of this embodiment, the threshold percent difference is 10% and system 120 detects or estimates a percentage of carbon dioxide (i.e., first fluid type) in the natural gas fuel based on the threshold difference exceeding 10%. As indicated above, in one embodiment, sensor 104 is a hot film mass flow sensor that operates, in part, based on design sensitivities which are responsive to the viscosity of the fluid being sensed, thermal conductivity of the fluid being sensed/measured, or both. Additionally, in this embodiment, sensor 105 is an orifice delta pressure mass flow rate measurement sensor that operates, in part, based on design sensitivities which are responsive to the molecular weight of the fluid being sensed. The illustrative embodiment of FIG. 4 shows that sensors 104, 105 of system 120 indicate relatively large sensor differences for natural gas fuels blended with $CO_2$ and relatively small sensor differences for natural gas fuels blended with propane blends. These differences are due, in part, to the fact that propane and carbon dioxide have essentially the same molecular weight, so an orifice delta pressure measurement cannot tell the difference between them. However, because propane and $CO_2$ have very different viscosities, a hot film flow rate measurement will react to propane and $CO_2$ differently. Thus, as shown in FIG. 4, when two sensors, each operating based on different principles, are used to sense/measure flow rate of an exemplary natural gas fuel, a percent difference in measured values will result which then may be utilized to detect the presence of a particular fluid type in the natural gas fuel.

Figure 5:
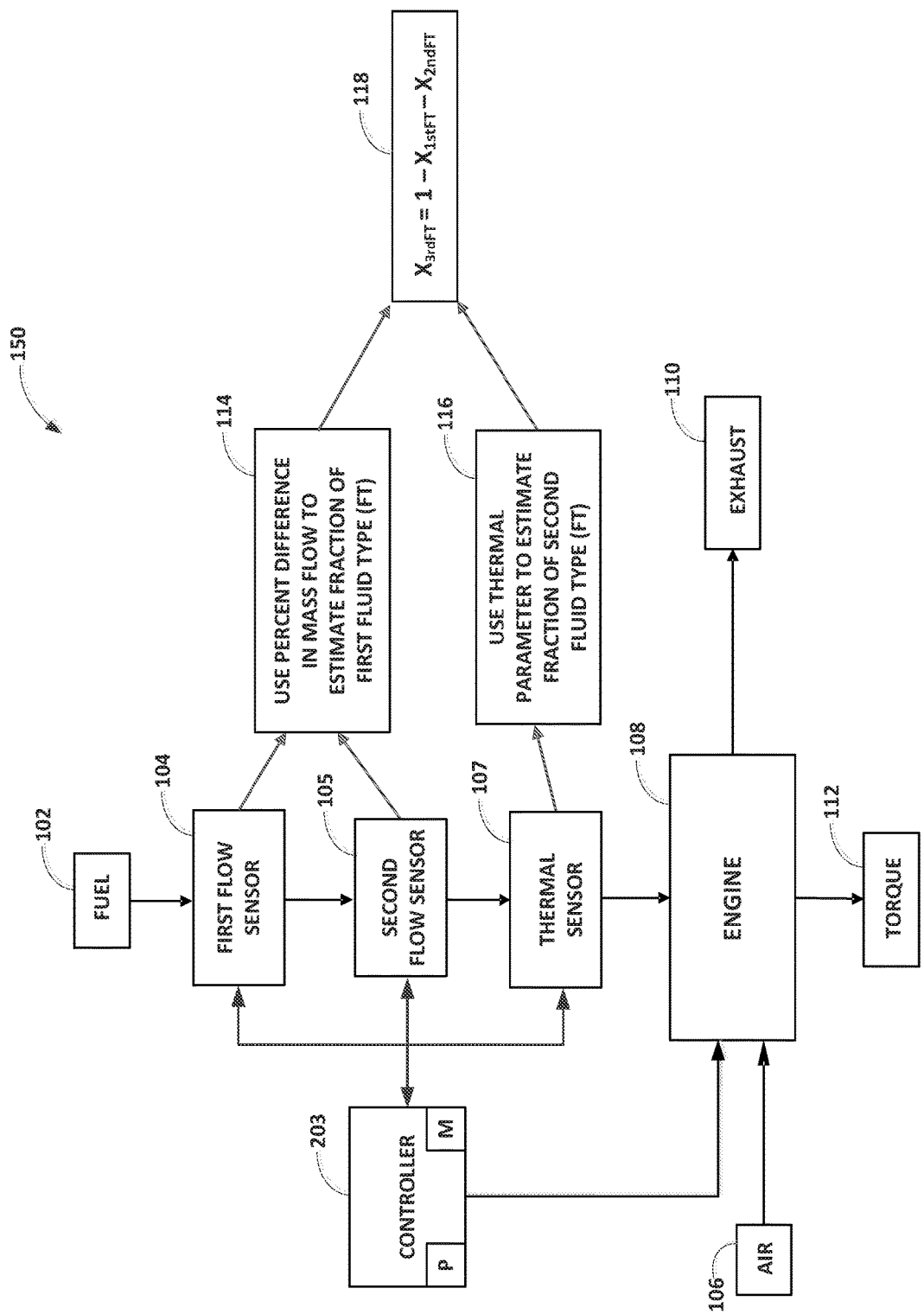
FIG. 5 is a block diagram of a fluid type prediction system comprising at least three sensors according to an embodiment of the present disclosure.

FIG. 5 is a block diagram of a fluid type prediction system comprising at least three sensors according to an embodiment of the present disclosure. Flow measuring system 150 (hereinafter "system 150") generally includes substantially the same components as system 120, except that system 150 includes first flow sensor 104, second flow sensor 105, and a third sensor 107. System 150 further includes first estimation block 114, second estimation block 116, and third estimation block 118. In one embodiment of the present disclosure, third sensor 107 provides a measurement of a characteristic of a particular fluid/fuel within the natural gas fuel supplied to engine 108, wherein the characteristic indicates a percentage of a second fluid type in the fluid. In one aspect of this embodiment, the characteristic is thermal conductivity of one or more constituents that comprise the fluid being sensed. In the illustrative embodiment of FIG. 5, third sensor 107 is an exemplary thermal sensor that measures the thermal conductivity of a fluid supplied to engine 108. Much like sensors 104, 105 described above, thermal sensor 107 is configured to provide one or more data/parameter signals to controller 203 that indicate the sensed/measured thermal conductivity of natural gas fuel used within engine 108.

In one embodiment, system 150 operates in the following manner; flow rate of natural gas fuel supplied to engine 108 is sensed/measured by sensor 104 and sensor 105 and controller 203 receives one or more parameter signals which indicate the flow rate value measured by the sensors. In this embodiment, memory M of controller 203 includes logic/instructions in the form of executable code that when executed by processor P causes the controller 203 to detect a percent difference between a mass flow rate measurement provided by sensor 104 and a mass flow rate measurement provided by second sensor 105. In the present disclosure, a certain percent difference will indicate the presence of at least a first fluid type in the fluid, namely, carbon dioxide. Controller 203 may further include logic that causes the controller to estimate the percentage/fraction of the $CO_2$ in the natural gas fuel based on or using the detected percent difference between the flow rate measurements provided by sensors 104 and sensor 105 (see estimation block 114). As discussed briefly above, controller 203 may then provide one or more control signals to engine 108 to adjust at least one performance characteristic of engine 108 in response to detecting a presence of the first fluid type in the natural gas fuel, in response to estimating the percentage/fraction of the $CO_2$ in the fuel, and/or in response to detecting the percent difference between the mass flow rate measurement provided by first sensor 104 and the mass flow rate measurement provided by second sensor 105.

Additionally, during operation of system 150, controller 203 may further receive one or more parameter signals indicating the thermal conductivity of one or more constituents that comprise the natural gas fuel. Likewise, in this embodiment, memory M of controller 203 includes logic/instructions in the form of executable code that when executed by processor P causes the controller 203 to detect the presence of and estimate the percentage/fraction of a second fluid type in the natural gas fuel based on or using the thermal conductivity measurement provided by second sensor 107 (see estimation block 116). More particularly, in the present disclosure, a certain thermal conductivity value corresponds to a certain percentage/fraction of methane in natural gas fuel. Thus, as described in more detail in the disclosed embodiment of FIG. 6, if the natural gas fuel supplied to engine 108 is comprised of methane, then the thermal conductivity parameter value provided by sensor 107 may be used to estimate the percentage/fraction of methane in the natural gas fuel. In one embodiment, controller 203 may provide one or more control signals to engine 108 to adjust at least one performance characteristic of engine 108 in response to detecting the presence of and/or estimating the percentage/fraction of the second fluid type (e.g., methane—$CH_4$ fraction) in the natural gas fuel.

As discussed above, an exemplary natural gas fuel composition includes methane, propane, and carbon dioxide. As also noted above, major constituent variations in the composition of natural gas fuels include changes in the amount of methane, propane, and carbon dioxide present in the fuel. In the illustrative embodiment of FIG. 5, estimation block 118 provides a straightforward equation wherein the percentage of the first fluid type (e.g., carbon dioxide—$CO_2$) and the percentage of the second fluid type (e.g., methane—$CH_4$) are used to determine a presence of a third fluid type (e.g., propane—$C_3H_8$) in the natural gas fuel and to determine or estimate a fraction/percentage of the third fluid type in the natural gas fuel. Accordingly, in one embodiment, controller 203 may further include logic that causes the controller to estimate the percentage/fraction of the first fluid type and the second fluid type and use these estimated fractions to determine a percentage/fraction of a third fluid type by using the equation of estimation block 118. Accordingly, system 150 may be used to determine the natural gas fuel composition by estimating the percentage/fraction of at least three distinct fluids that primarily comprise natural gas fuel. In one embodiment, controller 203 may provide one or more control signals to engine 108 to adjust at least one performance characteristic of engine 108 in response to determining the natural gas fuel composition by estimating the percentage/fraction of the at least three distinct fluids that primarily comprise natural gas fuel. In one aspect of this embodiment, the performance characteristic includes, for example, fuel injection timing, air-to-fuel ratio, charge flow rate and quantity, spark ignition timing, etc. In a variant of this aspect, adjusting the performance characteristic of engine 108 may include adjusting the operation of one or more components of engine 108.

Figure 6:
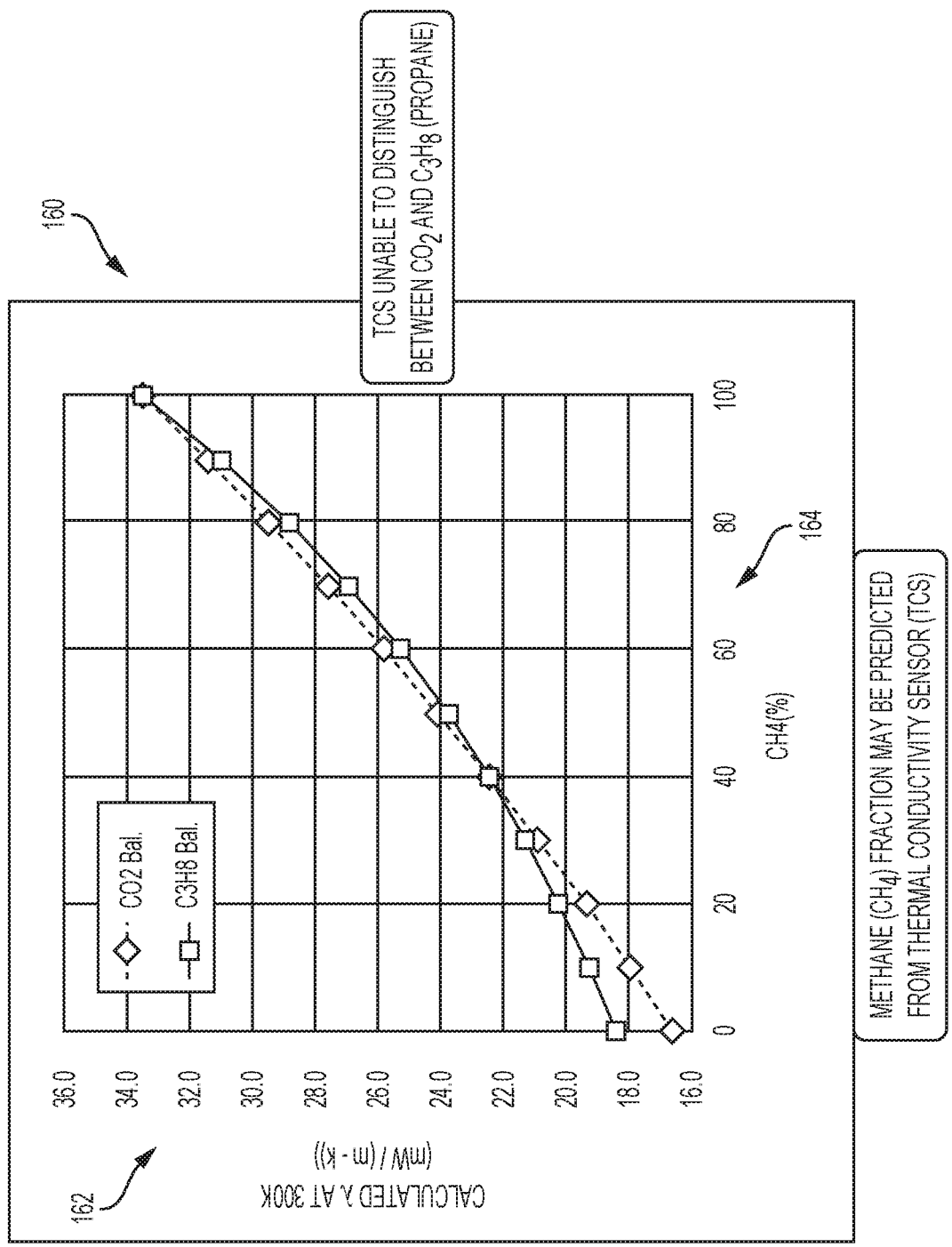
FIG. 6 is a graph that correlates sensor data to a second fluid percentage according to an embodiment of the present disclosure.

FIG. 6 is a graph 160 that correlates sensor data to a second fluid percentage according to an embodiment of the present disclosure. In the illustrative embodiment of FIG. 6, the sensor data is shown at Y-axis 162 and corresponds to a range of thermal conductivity values (in milliWatts per meters-Kelvin—(mW/(m-K)) that may be output by sensor 107 when sensor 107 is a thermal conductivity sensor. Likewise, X-axis 164 includes a range of second fluid percentage values that correspond to the thermal conductivity values of Y-axis 162 when the second fluid is methane—$CH_4$ gas. Propane ($C_3H_8$) and $CO_2$ have very similar thermal conductivity values, thus, for natural gas fuels that include some mixture of carbon dioxide and propane, a thermal conductivity sensor will generally output substantially the same values for each of these fluid types. As noted above, a certain thermal conductivity value corresponds to a certain percentage/fraction of methane—$CH_4$ in natural gas fuel. Thus, if natural gas fuel supplied to engine 108 is comprised of methane (in addition to $C_3H_8$ and $CO_2$), then the thermal conductivity parameter value provided by sensor 107 may be used to estimate the percentage/fraction of methane in the natural gas fuel.

Figure 7:
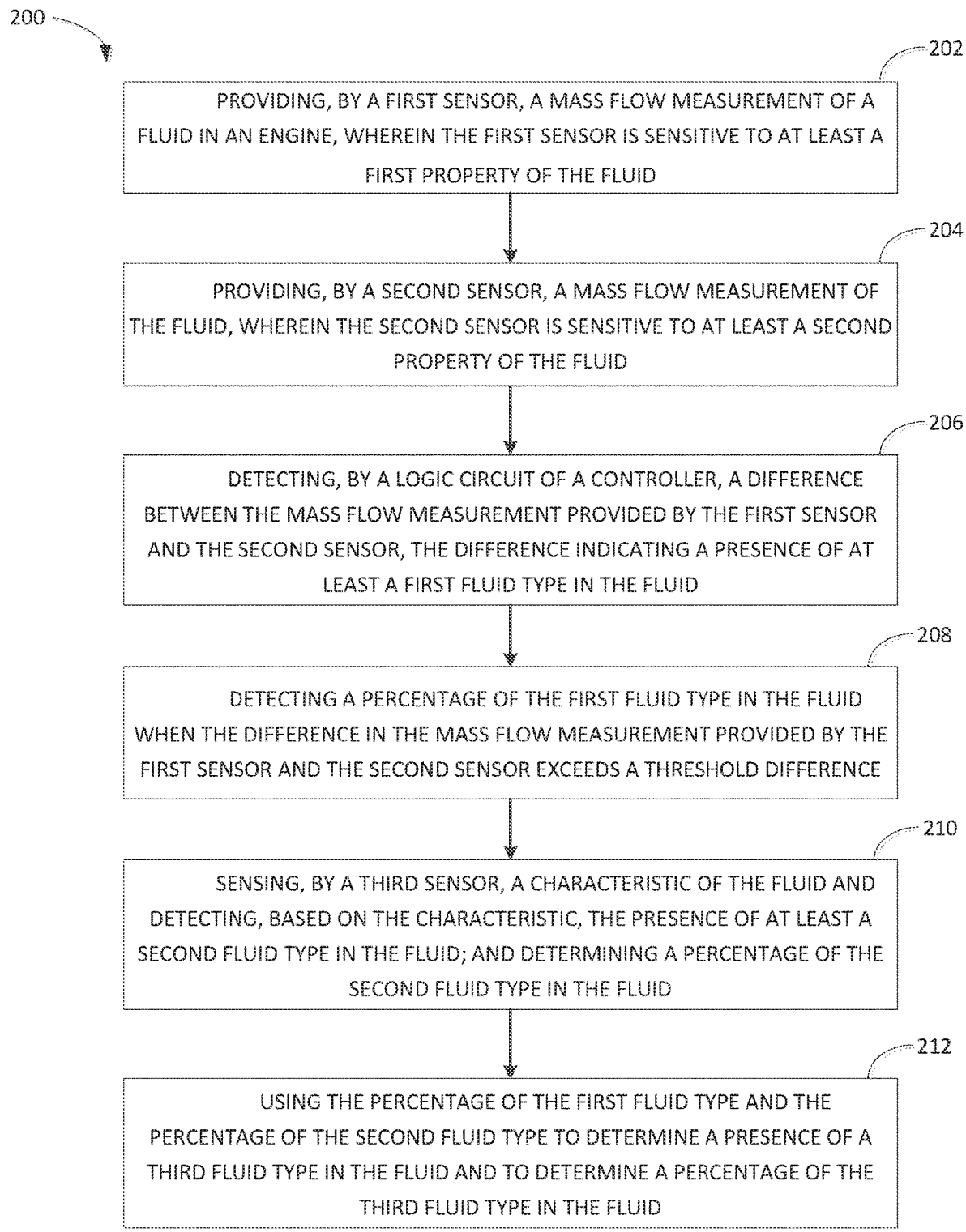
FIG. 7 is a flow diagram of an exemplary method for predicting a fluid type according to an embodiment of the present disclosure.

FIG. 7 is an exemplary flow diagram of a method 200 for predicting a fluid type in an exemplary natural gas fuel according to an embodiment of the present disclosure. In various embodiments, method 200 may be implemented and/or executed in a vehicle (or related engine application as described above) including at least one of system 120 and system 150. As such, a description of method 200 may reference the aforementioned components of system 120 and 150. Method 200 begins at block 202 and includes providing, by first sensor 104, a mass flow rate measurement of a fluid in engine 108, wherein the first sensor 104 is sensitive to at least a first property of the fluid. In one embodiment, the first fluid property may be at least one of the viscosity of the fluid and the thermal conductivity of the fluid. At block 204, method 200 further includes providing, by second sensor 105, a mass flow rate measurement of the fluid, wherein second sensor 105 is sensitive to at least a second property of the fluid. In one embodiment, the second fluid property may be the molecular weight of the fluid. At block 206, method 200 further includes detecting, by a logic circuit of controller 203, a difference between the mass flow rate measurement provided by first sensor 104 and second sensor 105, the difference indicating a presence of at least a first fluid type in the fluid. Method 200 further includes block 208 which detects a percentage of the first fluid type in the fluid when the difference in the mass flow measurement provided by first sensor 104 and second sensor 105 exceeds a threshold difference. At block 210, method 200 includes sensing, by third sensor 107, a characteristic of the fluid and detecting, based on the characteristic, the presence of at least a second fluid type in the fluid; and determining a percentage of the second fluid type in the fluid. In one embodiment, the characteristic is the thermal conductivity of the fluid being sensed. At block 212, method 200 includes using the percentage of the first fluid type and the percentage of the second fluid type to determine a presence of a third fluid type in the fluid and to determine a percentage of the third fluid type in the fluid.

As described herein, by analyzing mass flow rate measurements of delta pressure across an orifice and flow rate measurements from a hot film mass flow sensor, one can estimate the carbon dioxide—$CO_2$ fraction in natural gas fuel. Moreover, through the use of a thermal conductivity sensor one can estimate the methane—$CH_4$ fraction. The remainder would then be the propane—$C_3H_8$ fraction. The fluid detection and fraction estimation capabilities of systems 120 and 150 are achieved because the one or more sensors described herein have different sensitivities to molecular weight, thermal conductivity, and viscosity relative to the fluid being measured. Accordingly, a combination of two mass flow rate measurement sensors and one thermal conductivity sensor can be utilized to gain new information of natural gas fuel properties which allows for better control of an exemplary natural gas engine such as engine 108.

Through the teachings of the present disclosure, one of ordinary skill will understand, based on the detected natural gas fuel composition, whether changes in engine knocking conditions are from a change in fuel diluent level (i.e., CO2 blended in the natural gas fuel) or hydrocarbon content (i.e., propane blended in the natural gas fuel). With the additional knowledge of why engine knock has changed, one can react with the engine controls to improve engine performance and/or to adjust one or more performance characteristics of engine 108. Propane for example, increases engine knock but also has a higher lean limit. With knowledge of propane over less $CO_2$, one can operate the engine at leaner conditions to avoid or substantially mitigate the occurrence of engine knock. Moreover, since $CO_2$ is a diluent, similar to more fresh air 106 or recirculated exhaust gas (i.e., EGR), it is very beneficial to know how much $CO_2$ is included in the fuel and if the $CO_2$ content changes the vehicle operator might react differently than if the propane level changed. Therefore, having reliable information which indicates natural gas fuel composition and/or whether fuel quality is changing over time (or changing based on source location) is very useful for engine manufacturers. In exemplary engine control and natural gas fuel systems, reliable detection of the fuel composition aids in engine performance since optimal engine control and performance set points may be different for the diluent and hydrocarbon conditions.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage media include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs with minimal experimentation.

In the foregoing specification, specific embodiments of the present disclosure have been described. However, one of ordinary skill in the art will appreciate that various modifications and changes can be made without departing from the scope of the disclosure as set forth in the claims below. Accordingly, the specification and figures are to be regarded in an illustrative rather than a restrictive sense. The benefits, advantages, solutions to problems, and any element(s) that may cause any benefit, advantage, or solution to occur or become more pronounced are not to be construed as critical, required, or essential features or elements of any or all the claims. The invention is defined solely by the appended claims including any amendments made during the pendency of this application and all equivalents of those claims as issued. No claim element herein is to be construed under the provisions of 35 U.S.C. 112(f) unless the element is expressly recited using the phrase "means for."

We claim:

1. A fluid type prediction system, comprising:
a first sensor that provides a first mass flow measurement of a fluid in an engine, wherein the first sensor is sensitive to at least a first property of the fluid;
a second sensor that provides a second mass flow measurement of the fluid, wherein the second sensor is sensitive to at least a second property of the fluid; and
a controller configured to detect a difference between the first and the second mass flow measurements indicating a presence of at least a first fluid type in the fluid, and to adjust a performance characteristic of the engine in response to detecting the difference between the first and second mass flow measurements;
wherein the fluid is natural gas fuel, the first property is molecular weight, and the second property is at least one of viscosity and thermal conductivity.

2. The fluid type prediction system of claim 1, wherein the system is configured to detect a percentage of the first fluid type in the fluid in response to the difference between the first and second mass flow measurements exceeding a threshold difference.

3. The fluid type prediction system of claim 2, further comprising a third sensor that provides a measurement of a characteristic of the fluid, wherein the characteristic indicates a percentage of a second fluid type in the fluid.

4. The fluid type prediction system of claim 3, wherein the percentage of the first fluid type and the percentage of the second fluid type are used to determine a presence of a third fluid type in the fluid and to determine a percentage of the third fluid type in the fluid.

5. The fluid type prediction system of claim 3, wherein the first sensor is an orifice delta pressure mass flow sensor, the second sensor is a hot film mass flow sensor, and the third sensor is a thermal conductivity sensor.

6. The fluid type prediction system of claim 3, wherein the fluid is natural gas fuel comprising at least one of methane, propane, carbon dioxide, and combinations thereof, and the characteristic of the fluid is a thermal conductivity of the fluid.

7. The fluid type prediction system of claim 1, wherein the system is configured to estimate a percentage of one or more fluid types in the fluid.

8. A fluid type prediction system, comprising:
a controller comprising at least one processor and memory; and
a first interface coupled to the controller, the first interface configured to receive parameter signals corresponding to a mass flow measurement of a fluid in an engine, the parameter signals being provided by at least a first sensor and a second sensor;
wherein the memory comprises instructions that when executed by the at least one processor causes the controller to detect a difference between the mass flow measurement provided by the first sensor and the mass flow measurement provided by the second sensor, the difference indicating the presence of at least a first fluid type in the fluid, and to adjust a performance characteristic of the engine in response to detecting the difference between the mass flow measurements provided by the first and second sensors; and
wherein the first interface receives parameter signals provided by a third sensor, the parameter signals indicating a characteristic of the fluid, wherein the characteristic indicates a percentage of a second fluid type in the fluid.

9. The fluid type prediction system of claim 8, wherein the system is configured to detect a percentage of the first fluid type in the fluid in response to the difference between the mass flow measurements provided by the first sensor and the second sensor exceeding a threshold difference.

10. The fluid type prediction system of claim 8, wherein the first sensor is sensitive to at least a first property of the fluid and the second sensor is sensitive to at least a second property of the fluid.

11. The fluid type prediction system of claim 8, wherein the controller comprises a second interface configured to provide control signals to at least the first sensor and the second sensor to cause the first and second sensors to provide the mass flow measurement to the controller.

12. The fluid type prediction system of claim 10, wherein the fluid is natural gas fuel, the first property is molecular weight, and the second property is at least one of viscosity and thermal conductivity.

13. The fluid type prediction system of claim 8, wherein the controller uses the percentage of the first fluid type and the percentage of the second fluid type to determine a presence of a third fluid type in the fluid and to determine a percentage of the third fluid type in the fluid.

14. The fluid type prediction system of claim 8, wherein the first sensor is an orifice delta pressure mass flow sensor, the second sensor is a hot film mass flow sensor, and the third sensor is a thermal conductivity sensor.

15. A method for predicting a fluid type, comprising:
providing, by a first sensor, a mass flow measurement of a fluid in an engine, wherein the first sensor is sensitive to at least a first property of the fluid;
providing, by a second sensor, a mass flow measurement of the fluid, wherein the second sensor is sensitive to at least a second property of the fluid;
detecting, by a logic circuit of a controller, a difference between the mass flow measurement provided by the first sensor and the second sensor, the difference indicating a presence of at least a first fluid type in the fluid;
adjusting, by the logic circuit, a performance characteristic of the engine in response to detecting the difference between the mass flow measurement provided by the first sensor and the second sensor;
detecting a percentage of the first fluid type in the fluid in response to the difference in the mass flow measurement provided by the first sensor and the second sensor exceeding a threshold difference; and
sensing, by a third sensor, a characteristic of the fluid;
detecting, based on the characteristic, the presence of at least a second fluid type in the fluid; and
determining a percentage of the second fluid type in the fluid.

16. The method of claim 15, further comprising using the percentage of the first fluid type and the percentage of the second fluid type to determine a presence of a third fluid type in the fluid and to determine a percentage of the third fluid type in the fluid.

17. The method of claim 15, wherein the first sensor is an orifice delta pressure mass flow sensor, the second sensor is a hot film mass flow sensor, the third sensor is a thermal conductivity sensor, the first property is molecular weight, and the second property is at least one of viscosity and thermal conductivity.

18. A fluid type prediction system, comprising:
a controller comprising at least one processor and memory; and
an interface coupled to the controller, the interface configured to receive parameters indicating a mass flow measurement of a fluid in an engine;
wherein the memory comprises instructions that when executed by the at least one processor causes the controller to detect a difference between the mass flow measurement provided by a first sensor and the mass flow measurement provided by a second sensor, the difference indicating the presence of at least a first fluid type in the fluid;
wherein a performance characteristic of the engine is adjusted in response to the controller detecting a difference between the mass flow measurements provided by the first and second sensors;
wherein the parameters received by the interface are provided by at least the first sensor and the second sensor; and
wherein the interface is further configured to receive a measurement of a characteristic of the fluid, the characteristic indicating a percentage of a second fluid type in the fluid, and the measurement being provided by a third sensor.

19. The fluid type prediction system of claim 18, wherein the first sensor is an orifice delta pressure mass flow sensor, the second sensor is a hot film mass flow sensor, and the third sensor is a thermal conductivity sensor.

20. The fluid type prediction system of claim 18, wherein the system is configured to at least one of estimate a percentage of one or more fluid types in the fluid and detect a percentage of the first fluid type in the fluid in response to the difference between the first and the second mass flow measurements exceeding a threshold difference.

21. The fluid type prediction system of claim 18, wherein the performance characteristic includes at least one of fuel injection timing, air-to-fuel ratio, charge flow rate and quantity, spark ignition timing, and adjusting the operation of one or more components of the engine.

22. A fluid type prediction system, comprising:
a first sensor that provides a first mass flow measurement of a fluid in an engine, wherein the first sensor is sensitive to at least a first property of the fluid;
a second sensor that provides a second mass flow measurement of the fluid, wherein the second sensor is sensitive to at least a second property of the fluid;
a third sensor that provides a measurement of a characteristic of the fluid; and
a controller configured to detect a difference between the first and the second mass flow measurements, indicating a presence of at least a first fluid type in the fluid, and to adjust a performance characteristic of the engine in response to detecting the difference between the first and second mass flow measurements;
wherein the system is configured to detect a percentage of the first fluid type in the fluid in response to the difference between the first and second mass flow measurements exceeding a threshold difference; and
wherein the characteristic indicates a percentage of a second fluid type in the fluid.

23. The fluid type prediction system of claim 22, wherein the percentage of the first fluid type and the percentage of the second fluid type are used to determine a presence of a third fluid type in the fluid and to determine a percentage of the third fluid type in the fluid.

24. The fluid type prediction system of claim 22, wherein the first sensor is an orifice delta pressure mass flow sensor, the second sensor is a hot film mass flow sensor, and the third sensor is a thermal conductivity sensor.

25. The fluid type prediction system of claim 22, wherein the fluid is natural gas fuel comprising at least one of methane, propane, carbon dioxide, and combinations thereof, and the characteristic of the fluid is a thermal conductivity of the fluid.

26. A fluid type prediction system, comprising:
a controller comprising at least one processor and memory; and
a first interface coupled to the controller, the first interface configured to receive parameter signals corresponding to a mass flow measurement of a fluid in an engine, the parameter signals being provided by at least a first sensor and a second sensor;
wherein the memory comprises instructions that when executed by the at least one processor causes the controller to detect a difference between the mass flow measurement provided by the first sensor and the mass flow measurement provided by the second sensor, the difference indicating the presence of at least a first fluid type in the fluid, and to adjust a performance characteristic of the engine in response to detecting the difference between the mass flow measurements provided by the first and second sensors;
wherein the first sensor is sensitive to at least a first property of the fluid and the second sensor is sensitive to at least a second property of the fluid;
wherein the fluid is natural gas fuel, the first property is molecular weight, and the second property is at least one of viscosity and thermal conductivity.

\* \* \* \* \*